United States Patent [19]

Koizumi et al.

[11] 4,449,820
[45] May 22, 1984

[54] ZEEMAN ATOMIC ABSORPTION SPECTROPHOTOMETER

[75] Inventors: Hideaki Koizumi; Hideo Yamada, both of Katsuta; Kounosuke Oishi, Mito, all of Japan

[73] Assignee: Hitachi, Ltd., Tokyo, Japan

[21] Appl. No.: 299,109

[22] Filed: Sep. 3, 1981

[30] Foreign Application Priority Data

Sep. 24, 1980 [JP] Japan .............................. 55-131617

[51] Int. Cl.³ .......................................... G01N 21/72
[52] U.S. Cl. .................................... 356/307; 356/315; 364/498
[58] Field of Search ...................... 356/307, 315, 417; 364/498

[56] References Cited

U.S. PATENT DOCUMENTS

4,341,470  7/1982  Parker et al. ........................ 356/307
4,377,342  3/1983  Koizumi et al. ..................... 356/307

Primary Examiner—F. L. Evans
Attorney, Agent, or Firm—Antonelli, Terry & Wands

[57] ABSTRACT

A Zeeman atomic absorption spectrophotometer which monitors atomic absorption signals after a sample is introduced into the chemical flame atomizing portion. A signal peak value is measured in the portion of atomic absorption signals rising after the sample is introduced, or in the portion of atomic absorption signals breaking after the introduction of the sample is discontinued. A relation between the peak value and the sample concentration establishes a monovalent function. According to the conventional method, a relation between an average value of atomic absorption signals within a predetermined period of time and the concentration of specimen establishes a divalent function, and it is difficult to measure the samples, particularly in high-concentration regions. According to the present invention, however, it is possible to measure the samples of even high concentrations without having to dilute the samples.

14 Claims, 6 Drawing Figures

ZEEMAN ATOMIC ABSORPTION SPECTROPHOTOMETER

BACKGROUND OF THE INVENTION

The present invention relates to a Zeeman atomic absorption spectrophotometer.

Atomic absorption spectrophotometers have been widely used to quantitatively analyze metal elements contained in waste water, foods and urine. Among the atomic absorption spectrophotometers, an atomic absorption spectrophotometer which utilizes the Zeeman effect has high sensitivity and is capable of analyzing trace amounts of metals.

According to the Zeeman atomic absorptiometric method, a magnetic field of about 10 KG is applied to an atomized sample vapor, and the resonance absorption by atoms is measured by using two kinds of linearly polarized light with planes of polarization which intersect at right angles to each other. The polarized light (P //) having a plane of oscillation parallel with the magnetic field serves as a sample light beam, and the polarized light (P⊥) having a plane of oscillation perpendicular to the magnetic field serves as a reference light beam. This method is capable of precisely correcting the background absorption and features a very stable base line owing to its complete double beam method, and hence has drawn attention among many researchers in recent years as an extremely reliable and effective analytical method. The Zeeman effect can be utilized in several different ways. For example, in addition to the above-mentioned method by which the magnetic field of a predetermined intensity is applied to the sample vapor, the magnetic field may be applied to the light source, or the intensity of the magnetic field may be modulated. However, a problem which commonly develops in the Zeeman atomic absorptiometric methods is that the calibration curve drops in very high concentration regions.

The calibration curve drops and inverts in regions where the concentration is greater than a concentration $C_p$ which gives a maximum absorbance $A_p$. There is no problem with regard to the reliability of the measured values as long as the concentrations measured by the Zeeman atomic absorptiometric method are smaller than the concentration $C_p$. Since the calibration curve is given by a divalent function, however, an absorbance $A_1$ obtained by measuring an unknown sample does not guarantee that the sample concentration is $C_1$. There is also a possibility that the specimen concentration may be $C_2$ that is greater than $C_1$. As far as the calibration curve is given by a divalent function, it is quite impossible to determine whether it is $C_1$ or $C_2$ by the existing method. Furthermore, in regions of relatively high concentrations the calibration curve is so curved that it is difficult to analyze the concentrations with sufficient precision.

Theoretically, the drawback phenomenon can be explained as described below. Namely, according to the Zeeman atomic absorptiometric method of the type in which the magnetic field is applied to the sample atomizing portion, the background is corrected by using light from the light source which has the same plane of polarization as the component that does not undergo Zeeman split and light from the light source which has a right angle to the component, and a differential signal between the two components is obtained. In the high concentration regions, the absorption by the atoms saturates, whereas the background absorption increases linearly. Consequently, the differential signal is saturated, and inherently in the atomic absorptiometric method, a curving factor is added to the calibration curve giving rise to the occurrence of the drawback phenomenon.

It has been reported that a variety of types of Zeeman atomic absorptiometric methods can theoretically be realized, but in practice only one kind of Zeeman atomic absorption spectrophotometer has been produced in the world. This Zeeman atomic absorption spectrophotometer employs a graphite atomizer in a portion where the sample is to be atomized, consisting of a graphite tube and a power supply for supplying current to the tube. The sample is introduced into the tube and is atomized by the Joule heat produced by the electric current. U.S. patent application Ser. No. 236,995, filed Feb. 23, 1981, now U.S. Pat. No. 4,377,342, discloses a method which eliminates the above-mentioned drawback phenomenon inherent in the Zeeman atomic absorption spectrophotometer of this type.

The inventors of the present invention have also encountered the same problem during the course of developing a new Zeeman atomic absorption spectrophotometer using a chemical flame in the sample-atomizing portion.

In the generally employed atomic absorption spectrophotometer employing a chemical flame in the sample-atomizing portion, the absorbance signal during a predetermined period of time is averaged in order to remove noise which stems from the flame. The concentration is then found from the average value which takes the form of a divalent function.

SUMMARY OF THE INVENTION

The object of the present invention is to provide a Zeeman atomic absorption photometer of the type which employs chemical flame as a sample-atomizing portion, and which is capable of taking measurements even in high concentration regions.

Another object of the present invention is to provide a Zeeman atomic absorption spectrophotometer of the type which employs a chemical flame in the sample-atomizing portion, and which obtains correct concentration values even if the relation between the measured absorbance signal and the concentration may take the form of a divalent function.

The principle of the present invention is described below. In the atomic absorption using a flame (chemical flame), the sample is nebulized by a nebulizer and is introduced into the flame so that an atomic vapor is formed by thermal dissociation. The light from a hollow cathode lamp is permitted to pass through the atomic vapor to thereby measure the atomic resonance absorption. If observed over time, the atomic vapor is formed in the flame as mentioned below. Namely, when the sample is introduced into the nebulizer, the concentration of atomic vapor in the flame increases with time. Then, the concentration remains constant for a predetermined period of time while the sample is being introduced, and decreases with time after the introduction of the sample has been completed.

According to the present invention, peak values in the intensity of atomic absorption signals are measured while the concentration of atomic vapor is changing after the sample has been introduced into the atomizing portion.

According to the present invention, furthermore, the magnitudes of the peak value and of a value which is obtained by averaging the atomic absorption signals for a predetermined period of time are compared.

BRIEF DESCRIPTION OF THE DRAWINGS

FIGS. 1(a-c) is a diagram illustrating the principle according to the present invention;

DESCRIPTION OF THE PREFERRED EMBODIMENTS

Figure 1:
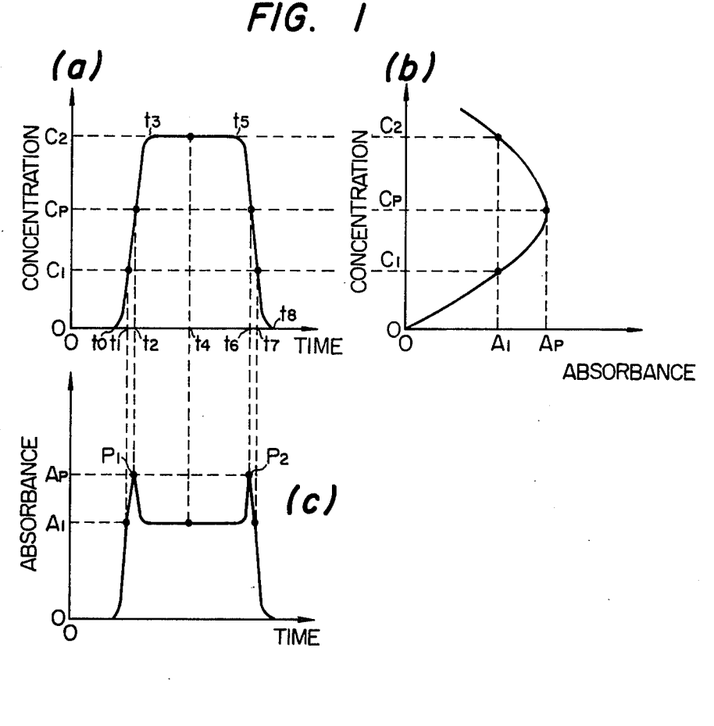
Figure 2:
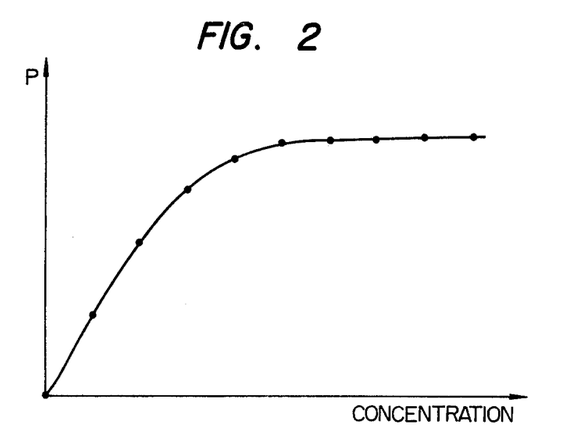
FIG. 2 is a diagram of a calibration curve according to an embodiment of the present invention.

The present invention will be explained below in conjunction with FIGS. 1 and 2.

FIG. 1(a) illustrates the relation between the concentration of atomic vapor in the flame and time. The time $t_0$ represents the moment at which the sample begins to be introduced. If the change in the concentration of atomic vapor is observed based on a scale of very short periods of time (0.5–0.1 second), the concentration of atomic vapor in the flame rises until a time $t_3$ and then remains constant. The concentration then starts to decrease from a time $t_5$ at which the absorption of the sample is completed and approaches zero at a time $t_8$. Thus, the vapor pressure of the sample increases and decreases presumably due to the fact that the sample which is nebiluzed in the nebulizer diffuses in the burner chamber. Experiment teaches that the concentration decreases more mildly than it increases.

FIG. 1(b) shows a calibration curve of Zeeman atomic absorption having the same axis of concentration as FIG. 1(a) illustrating the relation between the absorbance and the concentration in Zeeman atomic absorption. Referring to FIG. 1(a), it will be understood that the concentration of atomic vapor in the flame becomes $C_1$ at a time $t_1$. FIG. 1(b) teaches that the absorbance assumes a value $A_1$ when the concentration of atomic vapor is $C_1$. The thus found absorbance is shown in FIG. 1(c) which has the time axis in the same direction as that of FIG. 1(a). At a time $t_2$, the concentration is $C_p$ and the absorbance is the maximum value $A_p$. Thereafter, the absorbance decreases with the increase in concentration. The concentration assumes a constant value $C_2$ for a period of from time $t_3$ to time $t_5$. The absorbance $A_1$ observed during this period is smaller than the absorbance $A_p$, and the same value as when the concentration was $C_1$. From time $t_5$ to time $t_8$ at which the absorption is completed, the curve is just the reverse of when the absorption was initiated. The relation between the time and the absorbance possesses two peaks as shown in FIG. 1(c). In the case of a sample having a concentration greater than $C_p$, the absorbance at the time $t_4$ becomes smaller than $A_p$. However, peaks $P_1$ and $P_2$ which correspond to the maximum absorbance $A_p$ necessarily develop during the periods from $t_0$ to $t_3$ and $t_5$ to $t_8$. Experiment teaches that the peaks $P_1$ and $P_2$ last for such short periods of time that they cannot be correctly observed unless the response speed is faster than 0.2 second. The graph of FIG. 2 illustrates a relation between the sample concentration and the height of peak $P_2$ measured with a fast signal processing system, from which it is confirmed that the calibration curve is not inverted even in the high concentration regions and the analysis is properly effected relying upon the Zeeman atomic absorptiometric method.

An embodiment of the present invention will be explained below with reference to FIG. 3. First, the Zeeman atomic absorption spectrophotometer is briefly described. A source of light 10 is turned on by a current supplied from a power supply 12. The light emitted from the light source 10 falls on a polarizer 14. The light passing through the polarizer 14 is linearly polarized with particular plane of polarization. The polarizer 14 rotates, and the polarized plane of the linearly polarized light rotates correspondingly. The light from the polarizer 14 is then incident on an atomizing portion 16, which consists of a burner or the like that makes a flame, and is absorbed by the atoms. The atomizing portion 16 is placed in the magnetic field of about 10 KG established by a pair of magnets 18. Therefore, the atomic absorption line in the atomizing portion 16 is Zeeman-splitted. In the light which has passed through the atomizing portion 16, a predetermined wavelength is selected by a monochromator 20 and is allowed to fall on a detector 22 which produces electric signals that correspond to the intensity of the incident light. The electric signals are amplified by a pre-amplifier 24 and are converted into logarithmic quantities by a logarithmic converter 26. After noise components are removed by a band-pass filter 28 having a central frequency $f_1$, the signals are fed to a synchronized rectifier 30. Meanwhile, gate signals having a frequency $f_1$ synchronous with the rotation of the polarizer 14 are also fed from a gate circuit 32 to the synchronized rectifier 30. Therefore, the input signals are rectified by the synchronized rectifier 30. The output signals of the synchronized rectifier 30 exhibit absorbance that changes with time as shown in FIG. 1(c). The output signals are recorded by a recorder Rec.

Further, the light absorbance signals are fed to a peak discriminating circuit 40 which includes a timer 42 that feeds gate signals to a gate circuit for a predetermined period of time after the sample has been absorbed (for example, from $t_0$ to $t_3$ in FIG. 1(a)) or for a predetermined period of time after the sample has been introduced (for example, from $t_5$ to $t_8$ in FIG. 1(a)). Upon receipt of gate signals, the gate circuit 44 feeds absorbance signals to a peak holding circuit 46 which holds the peak value and inputs it to an absorbance concentration converter circuit 48, which correlates it with the calibration curve of FIG. 2, and produces a concentration value that corresponds to the absorbance that was introduced. The concentration value is indicated on an indicator 50 such as a meter or a printer. The peak holding circuit 46 holds either one of peaks $P_1$ or $P_2$ of FIG. 1(c). The precision, however, is better when peak $P_2$ is held because, as mentioned above, peak $P_2$ breaks more mildly than peak $P_1$ rises, and the signals can be processed more easily. Thus, it becomes possible to measure high concentrations.

The absorbance signals are also fed to a discriminating circuit 60 which includes the timer 42 that feeds gate signals to a gate circuit 62 for the period of time (for example, from $t_3$ to $t_5$ of FIG. 1(a)) in which the concentration of atomic vapor is maintained nearly constant in the flame. The gate circuit 62 is rendered conductive by the gate signals, and the absorbance signals are fed to an averaging circuit 64 which successively calculates average values of the input signals.

When the peak is discriminated by the peak holding circuit 46 and the averaging is finished by the averaging circuit 64, a comparator 66 compares the magnitude of the two outputs. The output of the peak holding circuit 46 is here denoted by $A_p$ and the output of the averaging circuit 64 by $A_1$. On the other hand, the output of the averaging circuit 64 is fed to the absorbance concentration converter circuit 68 which holds the calibration curve of the divalent function shown in FIG. 1(c). Therefore, when the output of the averaging circuit 64 is $A_1$, the converter circuit 68 selects either concentration $C_1$ or $C_2$. Here, when the comparator 66 produces an output under the condition $A_p$ is greater than $A_1$, the converter circuit 68 selects the concentration $C_2$ as the value which corresponds to the absorbance $A_1$, and the concentration $C_2$ is indicated on an indicator 70. The concentration is $C_1$ when the output of the comparator 66 indicates the fact that $A_p \leq A_1$. Further, when $A_p$ is greater than $A_1$, and when it is not required to measure such high concentrations, the error may be displayed on an indicator 72.

Figure 4:
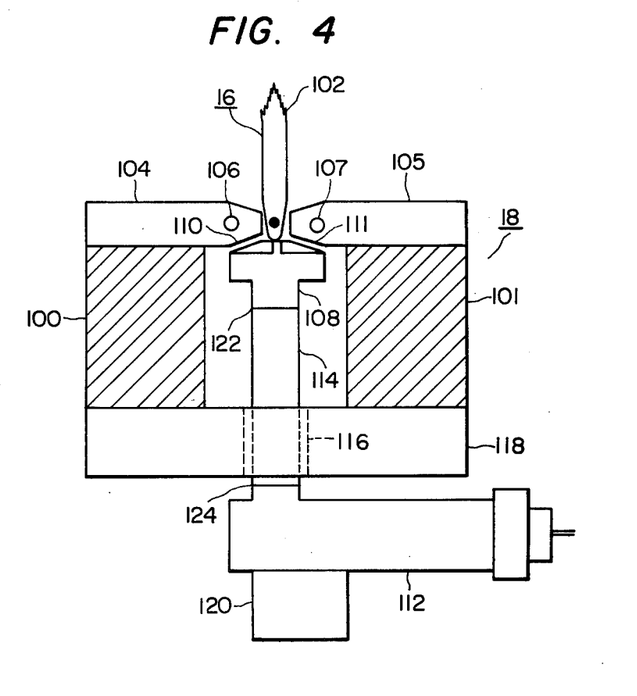
FIG. 4 is a view illustrating a portion of the embodiment of the present invention on an enlarged scale.

Application of the magnetic field to the burner is illustrated below with reference to FIG. 4. First, magnetic materials 100 and 101, which cannot be mechanically machined because of their small thermal resistance and brittleness, are disposed in such positions where they are separated from the flame 102 and do not receive heat radiation from the flame. The magnetic flux from the magnetic materials 100, 101 is applied to the flame via a magnetic circuit established by pole pieces 104, 105 made of a soft steel. Holes 106, 107 penetrate through the tips of pole pieces 104, 105 which come into direct contact with the flame 102, and water is made to flow through the holes 106, 107 to cool the pole pieces 104, 105. Further, the flame loses stability not only when a portion of the flame comes into contact with the cooled surfaces of the pole pieces but also when it is interfered by an external air flow. It has also been clarified through experiments that the secondary air plays an important role for maintaining stable combustion even when a pre-mixing type burner is used. Therefore, a clearance of at least 2 mm should be formed between the upper surface of burner head 108 and the lower surfaces of pole pieces 104, 105 symmetrically. Further, the angles of the upper surface of the burner head 108 should agree with the angles of the lower surfaces of the pole pieces 104, 105, so that the secondary air streams 110, 111 will flow smoothly and reach the nozzle without creating a disturbance. If the secondary air does not flow symmetrically toward the right and left sides, the flame is deflected toward the tip of one of the pole pieces. Further, if the amount of the secondary air is insufficient, the flame tends to flare and increase the noise level. In the case of a one-slot type pre-mixing burner, the flame can be stably established in a maximum gap of 6 mm by supplying the secondary air reliably. The positions of the cooling holes formed in the pole pieces also affect the intensity of the magnetic field established in the gap.

From the standpoint of cooling efficiency and the strength of the magnetic field, it is most effective to form the hole in a portion just before the thickness of the pole piece is to be reduced (in a portion 15 mm away from the tip of the pole piece), the hole having a diameter of one-third the thickness (18 mm) of the pole piece.

Owing to the above-mentioned setup, the flame can be stably established in the magnetic field as intense as 10 KG. A burner chamber (pre-mixing chamber) 112 is connected to burner head 108 through pipe 114. Pipe 114 runs through a hole 116 larger than pipe 114, formed in a lower yoke 118 of the magnet. The magnets are secured in a sample chamber, and the burner portion is installed on a plate 120 that is fastened to the sample chamber and that can be finely moved back and forth and up and down.

A stopper is provided to maintain a gap of 2 mm between the lower surfaces of the pole pieces and the upper surface of the burner head even when the burner is raised to its highest position. The burner efficiency is not decreased but rather is slightly increased when the total length of the pipe 114 connecting the burner chamber 112 to the burner head 108 is smaller than 20 cm. The burner head 108 and the pipe 114 are made of a paramagnetic metal (304 stainless steel or the like) so that they do not receive intense magnetic force from the magnets, otherwise it becomes difficult to move the burner position finely, the head is attracted by the magnets, or it becomes dangerous to attach or detach the head. The burner head will often have to be removed to clean its interior. Further, when the $H_2$-acetylene flame is to be formed, a head having a narrow slit must be used due to the difference in the rates of burning. Here, the whole burner is lowered, and the head 108 is pulled upward; i.e., the head 108 can be replaced. The connection portion 122 between the pipe 114 and the head 108 is sealed by an O-ring. The below-mentioned construction is effective when the sample chamber of the apparatus is particularly narrow. Namely, the burner chamber portion 112 is secured to the plate for fine movement. The magnets are placed on a rail, and are pulled toward the front of the sample chamber as required. The pipe 114 has a joint for connecting it to the head 108 as well as a joint 124 for connecting it to the chamber portion 112. To replace the burner, the plate 120 for fine movement is first fully lowered, and the pipe 114 is removed from the chamber 112. The magnets are then moved toward the front of the sample chamber.

According to the aforementioned optical system for the Zeeman atomic absorption spectrophotometer, a d-c magnetic field is applied to the atomizing portion, the direction in which the magnetic field is applied being at right angles with the axis of light. A variety of optical systems, however, have been known for the Zeeman atomic absorption spectrophotometer. For example, a magnetic field can be applied to the light source, the intensity of the magnetic field can be modulated, the direction in which the magnetic field is applied can be made parallel with the axis of light, or combinations of the methods. According to further modifications, the polarizer may be rotated or fixed, or the polarizer may be disposed in front of the detector. The embodiment of the present invention is effective for any of these optical systems.

Another embodiment of the present invention will be mentioned below with reference to FIG. 5, in which the same reference numerals as those of FIG. 3 denote the same members.

Figure 3:
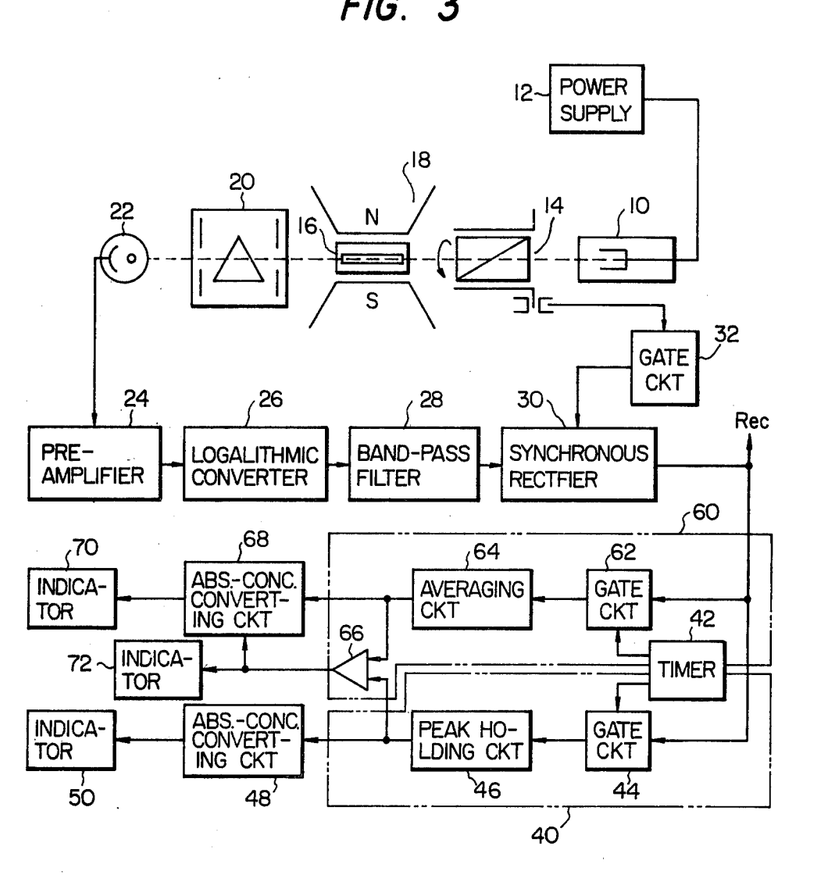
FIG. 3 is a block diagram according to an embodiment of the present invention.
Figure 5:
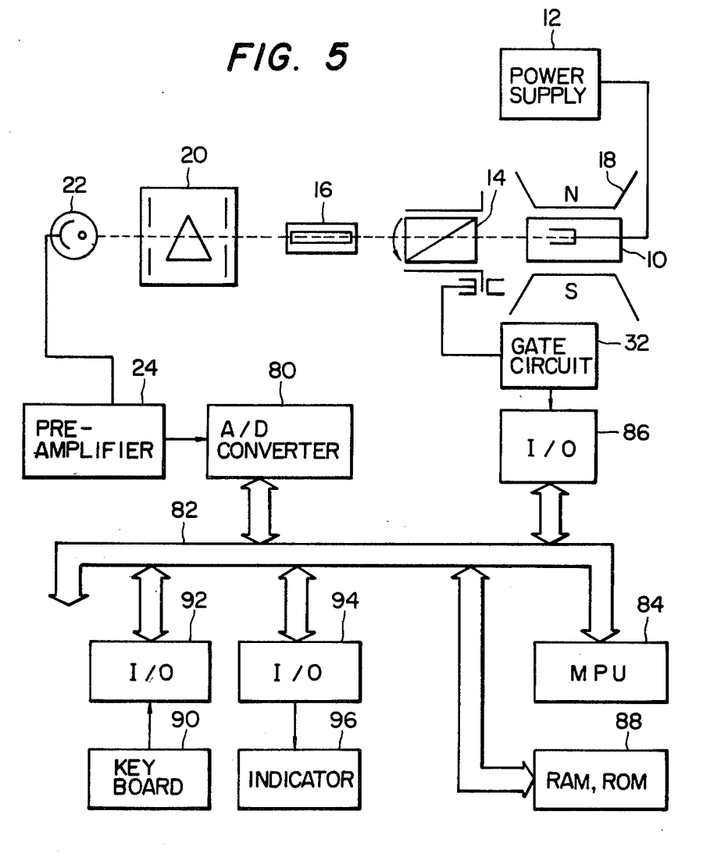
FIG. 5 is a block diagram according to another embodiment of the present invention.

The difference of the optical system of FIG. 5 from that of the embodiment of FIG. 3 resides in that the magnetic field produced by the magnet 18 is not applied to the atomizing portion but is applied to the source 10 of light. Therefore, the rays emitted from the source 10 of light are Zeeman-splitted. The $\pi$ component and the σ± component can be separated from each other using the polarizer 14 since they have different planes of polarization.

Figure 6:
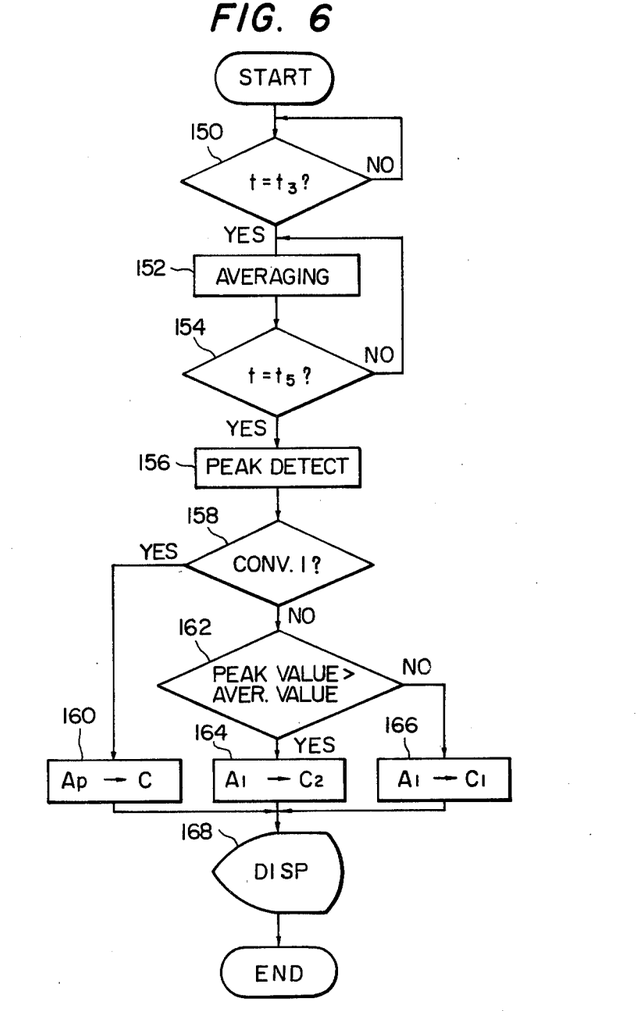
FIG. 6 is a flow chart of the embodiment of FIG. 5.

Another difference in the signal processing system resides in the use of a microprocessor MPU. The output of the detector 22 is amplified through the pre-amplifier 24 and is converted into a digital signal by an A/D converter 80. The digital signal is then fed to the MPU 84 through a bus line 82. Further, the gate signals from the gate circuit 32 are introduced through an input/output interface I/O 86. The absorbance is calculated in the MPU 84 relying upon the signals from the A/D converter 80. The absorbance signals are further corrected for their background by the gate signals. The program for finding the concentration from the absorbance of which the background is corrected has been stored beforehand in the ROM 88. The program will be illustrated below with reference to the flow chart of FIG. 6. As the sample is introduced into the burner, a discrimination step 150 monitors the lapse of time t. When the time t becomes $t_3$, for example, 2 seconds, the averaging operation is effected (processing 152). The averaging operation consists of introducing the absorbance data after every 20 milliseconds, followed by the averaging operation. The averaged results are stored in RAM 88. As a predetermined averaging time (2 to 10 seconds) is finished by a discrimination step 154, a point 156 introduces the absorbance data after every 20 milliseconds, successively compares the introduced data, and stores larger values in the RAM to measure a peak value. After the peak value is detected, a discrimination point 158 selects either the conversion method (Conv. 1 of the calibration curve of FIG. 2 or the conversion method (Conv. 2) of the calibration curve of FIG. 2, in order to convert the absorbance into the concentration. The selection is introduced, for example, from a keyboard through an I/O 92. When the Conv. 1 is selected, a step 160 calculates a concentration C that corresponds to the absorbance $A_p$. When the Conv. 2 is selected by the discrimination step 158, a step 162 discriminates which is the greater of the peak value and the average value. When the peak value is greater than the average value, a step 164 calculates a concentration $C_2$ which corresponds to the absorbance $A_1$. In other cases, a step 166 calculates a concentration $C_1$ that corresponds to the absorbance $A_1$. The value of concentration is displayed in a display step 168. The display is presented by a display unit 96 via an I/O 94.

According to the Zeeman atomic absorption spectrophotometer of the present invention as described above, it is possible to analyze the samples of concentrations higher than the concentrations that could be analyzed with the conventional instruments.

What is claimed is:

1. A Zeeman atomic absorption spectrophotometer comprising:
   a light source;
   an atomizing portion which is irradiated with light from the light source and where a sample is introduced into a chemical flame and atomized;
   a detector which receives the light from said light source after it has been absorbed by the atoms in the atomizing portion, and which converts the received light into electric signals;
   a magnet which applies the magnetic field to at least either one of said light source or said atomizing portion; and
   means for measuring peak values of signals of atomic absorption, which have been corrected for background absorption, while the concentration of sample vapor in the atomizing portion is changing after the sample has been introduced into said atomizing portion, and which measures the concentration of the sample by relying upon the peak values, said means for measuring including means for detecting peak values, means for obtaining a value of atomic absorption signals in the period after the sample has been introduced into said atomizing portion during which the concentration of sample vapor in said atomizing portion remains nearly constant, and means of obtaining concentration values corresponding to atomic absorption signals in response to the magnitudes of the peak values and the value of atomic absorption.

2. A Zeeman atomic absorption spectrophotometer according to claim 1, wherein said means for measuring the concentration comprises means for detecting peak values and a converter circuit which converts the absorbance into a concentration value that corresponds to the peak value.

3. A Zeeman atomic absorption spectrophotometer according to claim 1, wherein;
   said means for measuring concentration comprises a microprocessor associated with a random access memory and read-only memory;
   said read-only memory stores a program comprising;
   a step which calculates an average value of atomic absorption signals read within a period in which the concentration of sample vapor is nearly constant in the atomizing portion;
   a step which selects a maximum value among the atomic absorption signals read after the above step has been finished; and
   a step which calculates a concentration from either one of the average value or the maximum value based upon a setpoint from an external unit; and
   said microprocessor performs the calculation utilizing the memory area of the random access memory according to said program.

4. A Zeeman atomic absorption spectrophotometer according to claim 2 or 4, wherein the direction of the magnetic field produced by the magnet is at right angles with the optical axis.

5. A Zeeman atomic absorption spectrophotometer according to claim 4, wherein the intensity of the magnetic field produced by the magnet is constant.

6. A Zeeman atomic absorption spectrophotometer in accordance with claim 1 wherein said value of atomic absorption is an average value and said means of measuring concentration values utilizes either one of divalent concentration values corresponding to atomic absorption signals in response to the magnitudes of the peak values and the average value of atomic absorption.

7. A Zeeman atomic absorption spectrophotometer comprising:
   means for positioning an unknown sample on an optical axis, said unknown sample being atomized by a chemical flame;
   means which is positioned along the optical axis for directing light of a predetermined wavelength through vapor of the sample;
   means which shifts the wavelength of said light of the wavelength absorbed by the sample into Zeeman components;

means for detecting the light that has passed through the vapor of sample to produce an atomic absorption signal; and means for measuring a maximum value of the signals in a rising portion of atomic absorption signals when the sample is introduced into the chemical flame, and for measuring a maximum value of signals in a falling portion of atomic absorption signals when the sample is no longer introduced into the chemical flame.

8. A Zeeman atomic absorption spectrophotometer according to claim 7, wherein means for measurement comprises:

means which initiates operation simultaneously with the introduction of sample into the chemical flame and which generates signals for a predetermined period of time;

means for holding a maximum value of input signals; and gate means which is connected between the means for detecting and the holding means, which receives signals from said signal generating means, and which feeds the output of the means for detecting to the holding means.

9. A Zeeman atomic absorption spectrophotometer according to claim 7, further including means for obtaining a sample concentration from the measured value of said measuring means based upon a relation between the maximum value in the intensity of atomic absorption signals and the concentration of the sample.

10. A Zeeman atomic absorption spectrophotometer according to claim 7, wherein means are provided which calculate an average value of the intensity of atomic absorption signals detected by the detection means while the sample concentration in the chemical flame is stable.

11. A Zeeman atomic absorption spectrophotometer according to claim 7 wherein the means for measuring a maximum value comprises a programmed microprocessor associated with a memory which stores a program for calculating the maximum value, said microprocessor being coupled to the means for detecting to calculate the maximum value in response to the detected light, by utilization of said stored program during the time interval between the positioning of the sample in the optical axis and its dissipation from the optical axis.

12. A Zeeman atomic absorption spectrophotometer according to claim 8, 9, 10 or 11, wherein the direction of magnetic field produced by the magnet is at right angles with the optical axis.

13. A Zeeman atomic absorption spectrophotometer according to claim 12, wherein the intensity of magnetic field produced by the magnet is constant.

14. A Zeeman atomic absorption spectrophotometer in accordance with claim 10 further including means for obtaining a sample concentration as a function of the measured value of said measuring means, said means for obtaining a sample concentration including means responsive to the means which calculate an average value and the means for measuring maximum value for comparing the magnitude of the average value and the maximum value to detect when the peak value is greater than the average value to indicate when the maximum value during the falling portion of the absorption signals is present.

* * * * *